United States Patent
Lee et al.

(10) Patent No.: US 10,085,682 B2
(45) Date of Patent: Oct. 2, 2018

(54) APPARATUS AND METHOD OF MEASURING STRESS

(71) Applicant: SAMSUNG ELECTRONICS CO., LTD., Suwon-si (KR)

(72) Inventors: Joonhyung Lee, Yongin-si (KR); Sangkyu Kim, Yongin-si (KR); Seongho Cho, Gwacheon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 579 days.

(21) Appl. No.: 14/792,674

(22) Filed: Jul. 7, 2015

(65) Prior Publication Data

US 2016/0051175 A1 Feb. 25, 2016

(30) Foreign Application Priority Data

Aug. 25, 2014 (KR) .................. 10-2014-0110957

(51) Int. Cl.
- *A61B 5/1455* (2006.01)
- *A61B 5/16* (2006.01)
- *A61B 5/145* (2006.01)
- *A61B 5/00* (2006.01)

(52) U.S. Cl.
CPC ......... *A61B 5/165* (2013.01); *A61B 5/1455* (2013.01); *A61B 5/14546* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 6,292,686 B1 * | 9/2001 | Chaiken | A61B 5/0048 600/121 |
| 6,741,876 B1 | 5/2004 | Scecina et al. | |
| 2004/0127777 A1 * | 7/2004 | Ruchti | A61B 5/0071 600/316 |
| 2007/0118045 A1 * | 5/2007 | Naghavi | A61B 5/01 600/549 |
| 2012/0282636 A1 | 11/2012 | Altschul et al. | |

FOREIGN PATENT DOCUMENTS

| | | |
|---|---|---|
| JP | 3108765 B2 | 11/2000 |
| JP | 2002-534661 A | 10/2002 |
| JP | 2003-265445 A | 9/2003 |

* cited by examiner

*Primary Examiner* — Eric Winakur
*Assistant Examiner* — Marjan Fardanesh
(74) *Attorney, Agent, or Firm* — Sughrue Mion, PLLC

(57) ABSTRACT

Provided is an apparatus and method of measuring stress. The apparatus includes: a light source configured to emit light to the subject; a sensor configured to measure light reflected from the subject; a data extractor configured to obtain, from the reflected light, data that indicates at least one object material included in the subject; and a data processor configured to generate information about the stress of the subject based on a correlation between the obtained data and a reference value of stress.

19 Claims, 9 Drawing Sheets

APPARATUS AND METHOD OF MEASURING STRESS

CROSS-REFERENCE TO RELATED APPLICATION

This application claims priority from Korean Patent Application No. 10-2014-0110957, filed on Aug. 25, 2014 in the Korean Intellectual Property Office, the disclosure of which is incorporated herein by reference in its entirety.

BACKGROUND

1. Field

Exemplary apparatuses and methods relate to measuring a stress level by analyzing a change that occurs in a subject due to stress.

2. Description of the Related Art

In modern society, despite advancement in technology, people may be unhappy due to various stress factors. Stress not only reduces psychological happiness but also causes various diseases and physical damage. In particular, results of medical research have confirmed that chronic stress badly affects health. For example, chronic stress may worsen the immune system, increase the risk of infectious disease, and cause ulcers, sleep deprivation, depression, premature birth, underweight baby at birth, neural degeneration that induces impairment of learning and memory, elevation of blood pressure, cardiac complications, and heart rate variations due to high blood lipid levels.

Accordingly, interest in stress and stress-related illness has increased and thus attempts to numerically check stress have been made. For example, stress may be quantitatively checked by measuring a change in a concentration of a specific hormone in the blood. However, in this case, an invasive operation has to be performed, which may cause pain and anxiety.

SUMMARY

One or more exemplary embodiments provide apparatuses and methods of noninvasively measuring stress of a subject.

According to an aspect of an exemplary embodiment, an apparatus for measuring stress of a subject includes: a light source configured to emit light to the subject; a sensor configured to measure light reflected from the subject; a data extractor configured to obtain data that indicates at least one object material included in the subject from the reflected light; and a data processor configured to generate information about the stress of the subject based on a correlation between the obtained data and a reference value of stress.

The emitted light may have a wavelength within a range between about 2.5 μm and about 20 μm.

The sensor may be configured to measure a spectrum of the light reflected from the subject.

The at least one object material may include at least one selected from hyaluronic acid, triglyceride, wax ester, and squalene.

The data extractor may be configured to extract, from the spectrum, an absorbance of light in a first wavenumber range corresponding to the at least one object material.

The data extractor may perform normalization by dividing the absorbance of the light in the first wavenumber range by an absorbance at a second wavenumber that is outside the first wavenumber range.

The first wavenumber range may include at least one selected from a range from about 1640 $cm^{-1}$ to 1690 $cm^{-1}$, a range from about 1550 $cm^{-1}$ to about 1640 $cm^{-1}$, a range from about 1050 $cm^{-1}$ to about 1150 $cm^{-1}$, a range from about 1735 $cm^{-1}$ to about 1750 $cm^{-1}$, and a range from about 1620 $cm^{-1}$ to about 1680 $cm^{-1}$.

The reference value may correspond to a level of a hormone released by a living body under stress.

The hormone may include cortisol.

The data extractor may be further configured to obtain an intensity of the spectrum at a wavenumber obtained by Raman-shifting a wavenumber corresponding to the at least one object material.

The wavenumber corresponding to the at least one object material may include at least one selected from about 1625 $cm^{-1}$, 1418 $cm^{-1}$, 642 $cm^{-1}$, 1125 $cm^{-1}$, 1045 $cm^{-1}$, 948 $cm^{-1}$, 897 $cm^{-1}$, and 1625 $cm^{-1}$.

The apparatus may further include an attenuated total reflectance (ATR) layer that is disposed between the light source and the subject.

The sensor may include: a spectrometer configured to separate the reflected light according to wavelengths; and a detector configured to measure an intensity of the separated light.

The sensor may comprise a Fourier transform-infrared (FT-IR) spectrometer.

According to another aspect of an exemplary embodiment, a method of measuring stress of a subject includes: emitting light from a light source to the subject; measuring light reflected from the subject; obtaining data indicating at least one object material included in the subject from the reflected light; and generating information about the stress of the subject based on a correlation between the obtained data and a reference value of the stress.

The light may have a wavelength ranging from about 2.5 μm to about 20 μm.

The measuring of the light reflected from the subject may include measuring a spectrum of the light reflected from the subject.

The at least one object material may include at least one selected from hyaluronic acid, triglyceride, wax ester, and squalene.

The obtaining of the data may include extracting absorbance of light in a first wavenumber range corresponding to the at least one object material from the spectrum.

The extracting of the data may include performing normalization by dividing the absorbance of the light in the first wavenumber range by an absorbance at a second wavenumber that is outside the first wavenumber range.

The first wavenumber range may include at least one selected from a range from about 1640 $cm^{-1}$ to about 1690 $cm^{-1}$, a range from about 1550 $cm^{-1}$ to about 1640 $cm^{-1}$, a range from about 1050 $cm^{-1}$ to about 1150 $cm^{-1}$, a range from about 1735 $cm^{-1}$ to about 1750 $cm^{-1}$, and a range from about 1620 $cm^{-1}$ to about 1680 $cm^{-1}$.

The reference value may correspond to a level of a hormone by a living body under stress.

The hormone released due to the stress of the subject in the subject may include cortisol.

The extracting of the data may include obtaining an intensity of the spectrum at a wavenumber obtained by Raman-shifting a wavenumber corresponding to the at least one object material.

The wavenumber corresponding to the at least one object material may include at least one selected from about 1625 $cm^{-1}$, 1418 $cm^{-1}$, 642 $cm^{-1}$, 1125 $cm^{-1}$, 1045 $cm^{-1}$, 948 $cm^{-1}$, 897 $cm^{-1}$, and 1625 $cm^{-1}$.

The method may further include performing attenuated total reflectance (ATR) on the light reflected from the subject between the light source and the subject.

The measuring of the light reflected from the subject may include separating the light reflected from the subject according to wavelengths and measuring the light that is separated during the separating of the light reflected from the subject according to wavelengths.

The emitting of the light and the measuring of the light reflected from the subject may be performed by using Fourier transform-infrared (FT-IR) spectroscopy.

BRIEF DESCRIPTION OF THE DRAWINGS

The above and/or other aspects will be more apparent by describing certain exemplary embodiments, with reference to the accompanying drawings, in which.

DETAILED DESCRIPTION OF EXEMPLARY EMBODIMENTS

Figure 1:
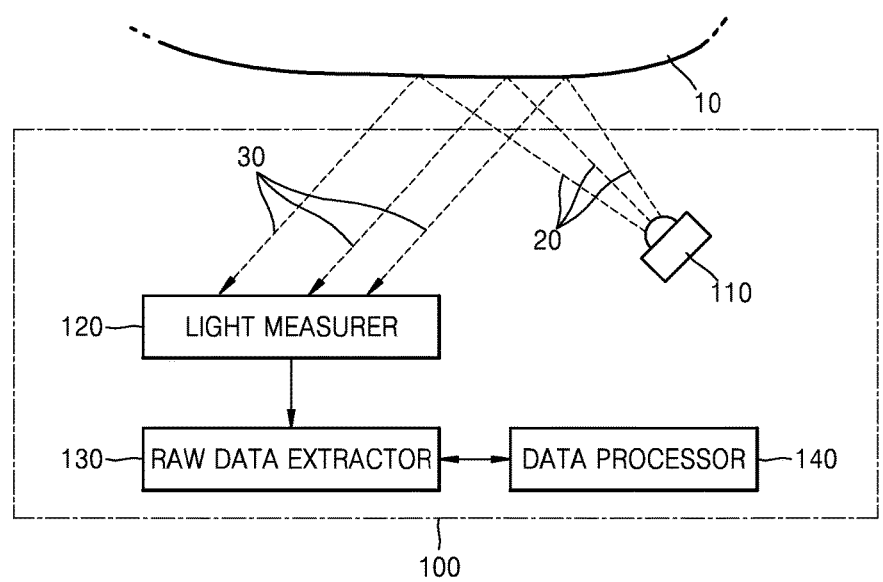
FIG. 1 is a view illustrating an apparatus for measuring stress, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items.

Expressions such as "at least one of," when preceding a list of elements, modify the entire list of elements and do not modify the individual elements of the list.

In the drawings, sizes or thicknesses of elements may be exaggerated for convenience of explanation. The following embodiments are exemplary and various modifications may be made from the exemplary embodiments. For example, it will also be understood that when a layer is referred to as being "on" or "over" another layer or a substrate, it may be directly on the other layer or the substrate, or intervening layers may also exist therebetween.

FIG. 1 is a view illustrating an apparatus 100 for measuring stress, according to an exemplary embodiment. Referring to FIG. 1, the apparatus 100 may include a light source 110 that emits light 20 to a subject 10, a light measurer 120 that measures light 30 reflected from the subject 10, and a data extractor 130 that extracts data related to at least one object material included in the subject 10 from information measured by the light measurer 120. The apparatus 100 may further include a data processor 140 that outputs information about stress of the subject 10. The data processor 140 may output the information about the stress by using a correlation between the data and the stress of the subject 10. The light measurer 120 and the data extractor 120 may be implemented as a sensor. In another example, only the light measurer 120 may be implemented as a sensor, and all the operations of the data extractor 130 may be performed by the data processor 140. In that case, the apparatus 100 includes the light measurer 120 (i.e., sensor) and the data processor 140 which incorporates the data extractor 130.

The subject 10 that is a subject to be examined may be a living body, for example, a human or an animal. The light source 110 may emit light having a wavelength or a range of wavelengths. The light source 110 may emit visible light or infrared light, or may be a laser source that emits light having a single wavelength or a narrow range of wavelengths. If the light source 110 emits light having a single wavelength, the light source 110 may emit a plurality of pieces of light having various wavelengths a number of times in order to obtain an absorption spectrum. In this case, whenever the light source 110 emits the light 20, the light measurer 120 may measure an intensity of the light 30 reflected from the subject 10. However, the light source 110 is exemplary and is not limited thereto, and thus may be selected in various ways according to characteristics according to an interaction between the light 20 and the subject 10.

A wavelength band of the light 20 that is emitted from the light source 110 may be selected in various ways. For example, the light 20 may include infrared light. The light 20 may include mid-infrared light. For example, the light 20 may include a wavelength band ranging from about 2.5 μm to about 20 μm. However, the light 20 is exemplary, and the present exemplary embodiment is not limited thereto. For example, the light 20 may be near-infrared light or far infrared light. For example, the light 20 may include a wavelength band ranging from about 1 μm to about 2.5 μm. For example, the light 20 may include a wavelength band ranging from about 0.5 μm to about 1 μm. Alternatively, the light 20 may include a wavelength band ranging from about 20 μm to about 1000 μm.

Figure 2:
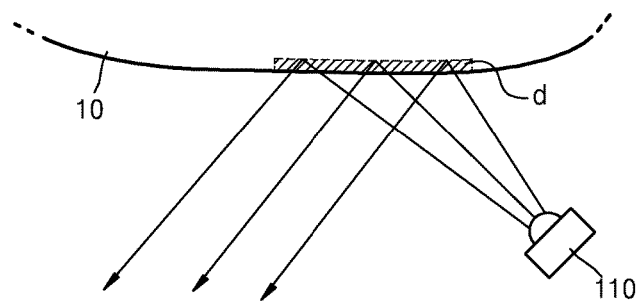
FIG. 2 is a view illustrating a case in which light penetrates a subject.

The light 20 may penetrate the subject 10 to a predetermined depth before being reflected from the subject 10. FIG. 2 is a view illustrating a case in which the light 20 penetrates the subject 10.

Referring to FIG. 2, the light 20 penetrates the subject 10 to a penetration depth d before being reflected by the subject 10. Although the light 20 penetrates the subject 20 to the penetration depth d in FIG. 2, part of the light 20 may penetrate to a depth less than the penetration depth d and another part of the light 20 may penetrate to a depth greater than the penetration depth d. The penetration depth d may vary according to a wavelength band of the light 20. For example, when the light 20 has a short wavelength, the light 20 has high energy and thus may penetrate the subject 10 to a relatively deep penetration depth, and when the light 20 has a long wavelength, the light 20 has low energy and thus may penetrate the subject 10 to a relatively shallow penetration depth.

For example, mid-infrared light may have a penetration depth ranging from about 50 μm to about 100 μm. Accordingly, the mid-infrared light may be used to analyze an epidermis layer of the skin of the subject 10. Also, since the mid-infrared light has a sharper spectrum peak than near-infrared light, a specific component may be more easily quantified through spectrum analysis. The mid-infrared light may be effectively used to analyze the epidermis layer of the skin of the subject 10.

Figure 3:
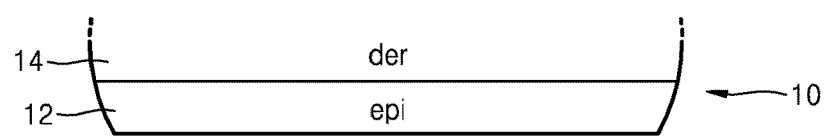
FIG. 3 is a view illustrating a layer structure of the skin of the subject.

FIG. 3 is a view illustrating a layer structure of the skin of the subject 10.

Referring to FIG. 3, the skin of the subject 10 includes an epidermis layer 12 and a dermis layer 14. The epidermis layer 12 that is an epithelial tissue of the skin may have a thickness that varies according to a position of the subject 10. However, in general, the thickness of the epidermis layer 12 may be tens of μm. Accordingly, when the epidermis layer 12 is to be analyzed, the light 20 that is mid-infrared light whose penetration depth is small may be used. The dermis layer 14, instead of the epidermis layer 12, may need to be analyzed. In this case, near-infrared light may be used.

Figure 4:
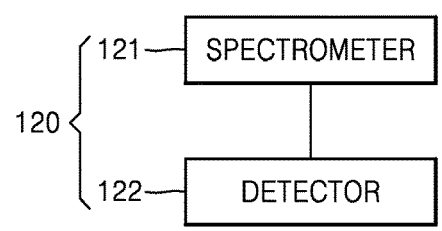
FIG. 4 is a view illustrating a light measurer.

Referring to FIG. 1, the light measurer 120 may measure the light 30 reflected from the subject 10. The light measurer 120 may measure an intensity of the light 30 reflected from the subject 10 according to wavelengths. Referring to FIG. 4, the light measurer 120 may include a spectrometer 121 that separates the light 30 reflected from the subject 10 according to the wavelengths and a detector 122 that measures an intensity of the light 30 that is split by the spectrometer 121 according to wavelengths. Thus, the detector 122 measure the intensity of the light 30 reflected from the subject 10 according to wavelengths. The spectrometer 121 may be a general device that separates the light 30 reflected from the subject 10 according to wavelengths. For example, the spectrometer 121 may be a prism spectrometer, a grating spectrometer, or an interference spectrometer. However, the spectrometer 121 is exemplary and the present exemplary embodiment is not limited thereto. Also, the detector 122 may be a general light sensor that receives the light 30 reflected by the subject 10 and measures an intensity of the light 30. The detector 122 may be a device that converts the light 30 into an electrical signal and detects the electrical signal.

When the light measurer 120 measures the intensity of the light 30 reflected from the subject 10 according to wavelengths, an absorption spectrum that is the fraction of the light 20 absorbed by the subject 10 may be analyzed by using the intensity of the light reflected from the subject 10 according to wavelengths. The absorption spectrum may be a spectrum curve showing an absorbance of the subject 10 according to a wavelength of the light 20. The absorption spectrum may be derived from a difference between a spectrum of the light 20 that is emitted from the light source 110 and a spectrum of the light 30 that is reflected from the subject 10.

The data extractor 130 may extract data related to at least one object material included in the subject 10 from the absorption spectrum. The object material may be a material released into the skin or other tissue of the subject 10 and an amount of the object material changes according to a stress level of the subject 10. When the subject 10 is under stress, the amount of the object material may be changed due to a hormone released into the blood or the body fluid of the subject 10. The hormone released into the blood or the body fluid of the subject 10 may include cortisol. The object material may include at least one selected from hyaluronic acid, triglyceride, wax ester, and squalene. Information about the object material may include, for example, a concentration of the object material.

Hyaluronic acid is a natural material that is produced in a living body naturally and is generally found in the skin of a human or an animal. Hyaluronic acid functions to moisturize the skin. A concentration of hyaluronic acid in the subject 10 may decrease as a concentration of cortisol increases. Triglyceride, wax ester, and squalene are materials included in oil that is released in the skin of the subject 10. The amount of oil released in the skin of the subject 10 may increase as a concentration of cortisol increases. Accordingly, concentrations of triglyceride, wax ester, and squalene may also increase. The object materials are exemplary, and the present exemplary embodiment is not limited thereto.

The data may be data in which an interaction between the object material and the light 20 that is emitted from the light source 110 is reflected. For example, the data may be obtained from a relationship between an intensity of light and a wavelength or a wavenumber of the light. For example, information about a reference wavelength or a reference wavenumber corresponding to a specific material or a specific molecular structure (functional group) in an absorption spectrum is already known. Data about the specific material or the specific molecular structure may be extracted by measuring an intensity of light with respect to the reference wavelength or the reference wavenumber. By using this principle, an intensity of the absorption spectrum in a first wavenumber range corresponding to the at least one object material may be obtained as the data. The first wavenumber range may be a wavenumber range in which the object material easily absorbs the light 20. For example, the first wavenumber range may vary according to a chemical functional group included in the object material. For example, the first wavenumber range may be selected to include at least one selected from a range about 1640 $cm^{-1}$ to about 1690 $cm^{-1}$, a range from about 1550 $cm^{-1}$ to about 1640 $cm^{-1}$, a range from about 1050 $cm^{-1}$ to about 1150 $cm^{-1}$, a range from about 1735 $cm^{-1}$ to about 1750 $cm^{-1}$, and a range from about 1620 $cm^{-1}$ to about 1680 $cm^{-1}$. The first wavenumber range is exemplary, and the present exemplary embodiment is not limited thereto. An absorbance of the absorption spectrum in the first wavenumber range may be extracted as the data.

Figure 5:
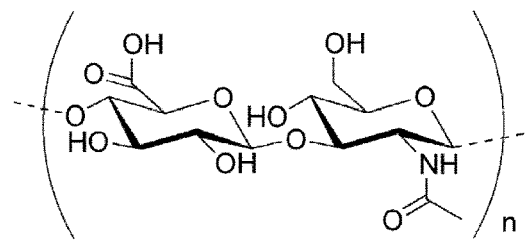
FIG. 5 is a view illustrating a molecular structure of hyaluronic acid.

FIG. 5 is a view illustrating a molecular structure of hyaluronic acid.

Referring to FIG. 5, hyaluronic acid is formed of N-acetylglucosamine and glucuronic acid that are linked via alternating β-1,4 and β-1,3 glycosidic bonds. As shown in FIG. 5, hyaluronic acid includes a functional group C=O, a functional group N—H, and a functional group C—O. The light measurer 10 may measure an absorbance of an absorption spectrum in a wavenumber range in which the functional groups C=O, N—H, and C—O selectively absorb the light 20. The first wavenumber range may include a wavenumber range corresponding to hyaluronic acid.

For example, a wavenumber range from about 1640 cm$^{-1}$ to about 1690 cm$^{-1}$ may correspond to the functional group C=O, a wavenumber range from about 1550 cm$^{-1}$ to about 1640 cm$^{-1}$ may correspond to the functional group N—H, and a wavenumber range from about 1050 cm$^{-1}$ to about 1150 cm$^{-1}$ may correspond to the functional group C—O. Accordingly, information about a change in a concentration of hyaluronic acid in the subject 10 may be extracted by checking a change in an absorbance of a spectrum peak in these ranges. Although three wavenumber ranges are exemplarily used in order to detect a change a concentration of hyaluronic acid, the present exemplary embodiment is not limited thereto and any wavenumber range that may be adopted by one of ordinary skill in the art may also be used in the exemplary embodiment. Also, all or some of the wavenumber ranges may be considered.

Figure 6:
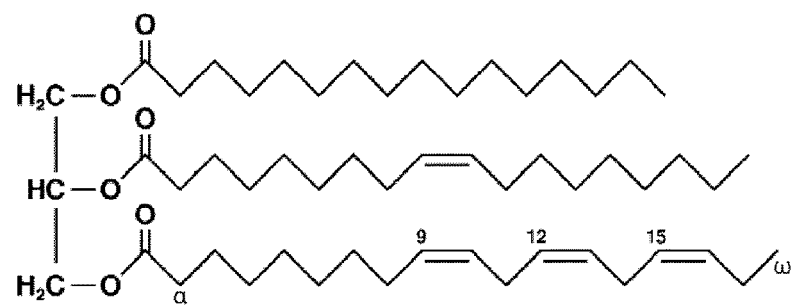
FIG. 6 is a view illustrating a molecular structure of triglyceride.

FIG. 6 is a view illustrating a molecular structure of triglyceride.

Referring to FIG. 6, triglyceride is an ester formed by combining glycerol with three fatty acid molecules. As shown in FIG. 6, triglyceride includes an ester functional group, a functional group C—O, and a functional group C=C. For example, a first wavenumber range corresponding to the ester functional group may include a range from about 1735 cm$^{-1}$ to about 1750 cm$^{-1}$, a first wavenumber range corresponding to the functional group C—O may include a range from about 1050 cm$^{-1}$ to about 1150 cm$^{-1}$, and a first wavenumber range corresponding to the functional group C=C may include a range from about 1620 cm$^{-1}$ to about 1680 cm$^{-1}$. Information about a change in a concentration of triglyceride in the subject 10 may be extracted by checking a change in an absorbance of a spectrum peak in these wavenumber ranges. Although the three wavenumber ranges are used in order to detect a change in a concentration of triglyceride, the present exemplary embodiment is not limited thereto and any wavenumber range that may be adopted by one of ordinary skill in the art may be used in the exemplary embodiment. Also, all or some of the wavenumber ranges may be considered.

Figure 7:
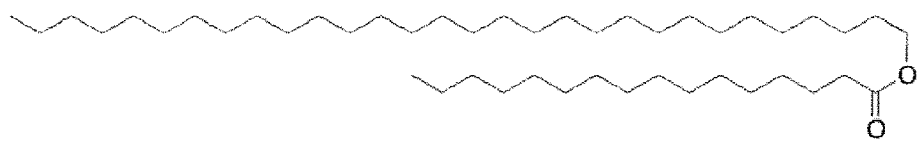
FIG. 7 is a view illustrating a molecular structure of wax ester.

FIG. 7 is a view illustrating a molecular structure of wax ester.

Referring to FIG. 7, wax ester is an ester formed of a fatty acid and a fatty alcohol. As shown in FIG. 7, wax ester may include an ester functional group and a functional group C—O. For example, a first wavenumber range of the ester functional group may include a range from about 1735 cm$^{-1}$ to about 1750 cm$^{-1}$ and a first wavenumber range of the functional group C—O may include a range from about 1050 cm$^{-1}$ to about 1150 cm$^{-1}$. Information about a change in a concentration of wax ester in the subject 10 may be extracted by checking a change in an absorbance of a spectrum peak in the ranges. Although the two wavenumber ranges are exemplarily used in order to detect a change in a concentration of wax ester, the present exemplary embodiment is not limited thereto and any wavenumber range that may be adopted by one of ordinary skill in the art may be used in the exemplary embodiment. Also, all or some of the wavenumber ranges may be considered.

Figure 8:
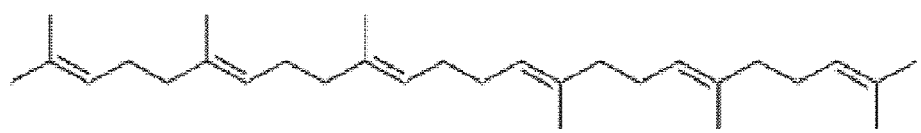
FIG. 8 is a view illustrating a molecular structure of squalene.

FIG. 8 is a view illustrating a molecular structure of squalene.

Referring to FIG. 8, squalene is a natural 30-carbon organic compound. As shown in FIG. 8, squalene includes a functional group C=C. A first wavenumber range of the functional group C=C may include a range from about 1620 cm$^{-1}$ to about 1680 cm$^{-1}$. Accordingly, information about a change in a concentration of wax ester in the subject 10 may be extracted by checking a change in an absorbance of a spectrum peak in the range. The wavenumber range is exemplary, and the present exemplary embodiment is not limited thereto.

Figure 9:
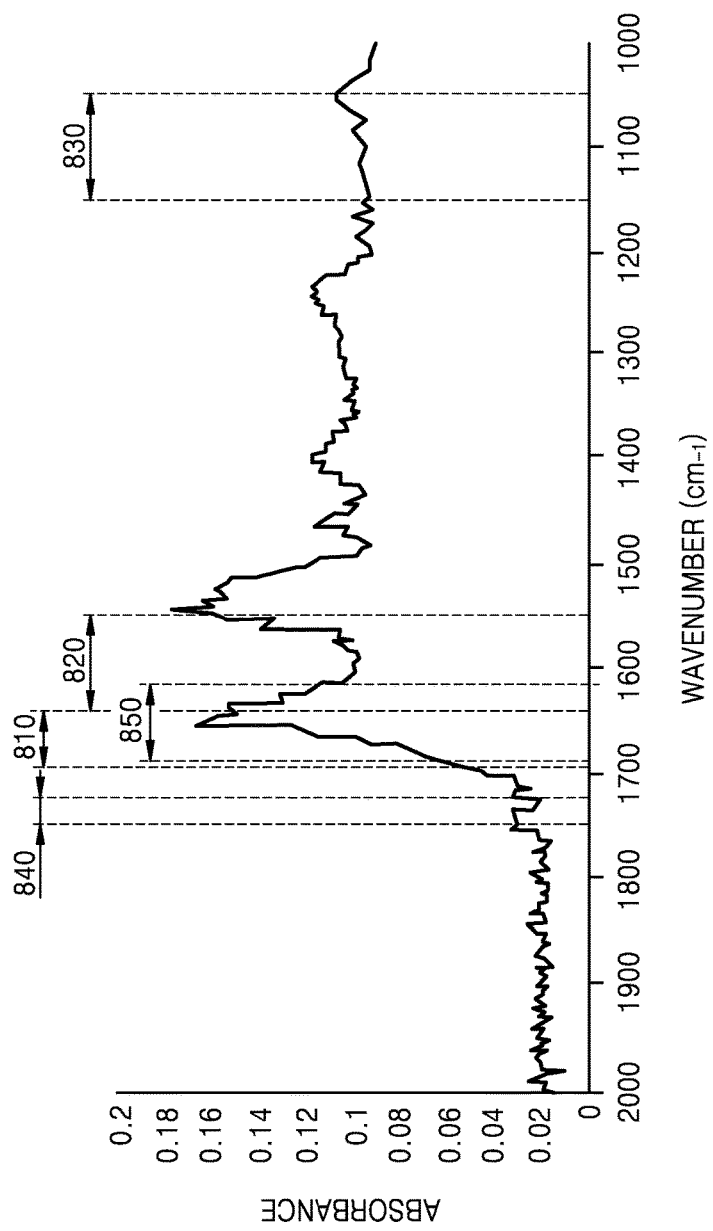
FIG. 9 is a view illustrating a result of an absorption spectrum obtained by the light measurer.

FIG. 9 is a view illustrating a result of an absorption spectrum obtained by the light measurer 120.

FIG. 9 shows that a plurality of peaks that have higher absorbances than adjacent other points in the absorption spectrum. The data extractor 130 may extract data from the absorbances of the peaks formed in a first wavenumber range. The first wavenumber range of FIG. 9 may include a range 810 from about 1640 cm$^{-1}$ to about 1690 cm$^{-1}$, a range 820 from about 1550 cm$^{-1}$ to about 1640 cm$^{-1}$, a range 830 from about 1050 cm$^{-1}$ to about 1150 cm$^{-1}$, a range 840 from about 1735 cm$^{-1}$ to about 1750 cm$^{-1}$, and a range 850 from about 1620 cm$^{-1}$ to about 1680 cm$^{-1}$. The first wavenumber range may be selected in consideration of chemical functional groups of hyaluronic acid, triglyceride, wax ester, and squalene that may be included in an object material. The wavenumber ranges and the object materials of FIG. 9 are exemplary and various modifications may be made from the wavenumber ranges and the object materials by one of ordinary skill in the art in the exemplary embodiment.

The absorption spectrum of FIG. 9 itself may be used to extract data. However, the absorption spectrum may be used after being processed by the data extractor 130 through normalization. The reason why the normalization is performed is as follows. An absorbance of the absorption spectrum may vary due to other factors irrespective of a concentration of an object material. For example, the absorbance may vary according to a distance between the light source 110 and the subject 10, or according to a change in a contact pressure or an intensity of the light 20 that is emitted from the light source 110 when the light source 110 and the subject 10 contact each other. Accordingly, accuracy may be reduced when information about a concentration of the object material is extracted by using the absorbance of the absorption spectrum peak. However, relative heights of peaks to other points in the absorption spectrum are not greatly changed due to a position of the light source 110 or other factors.

Figure 10:
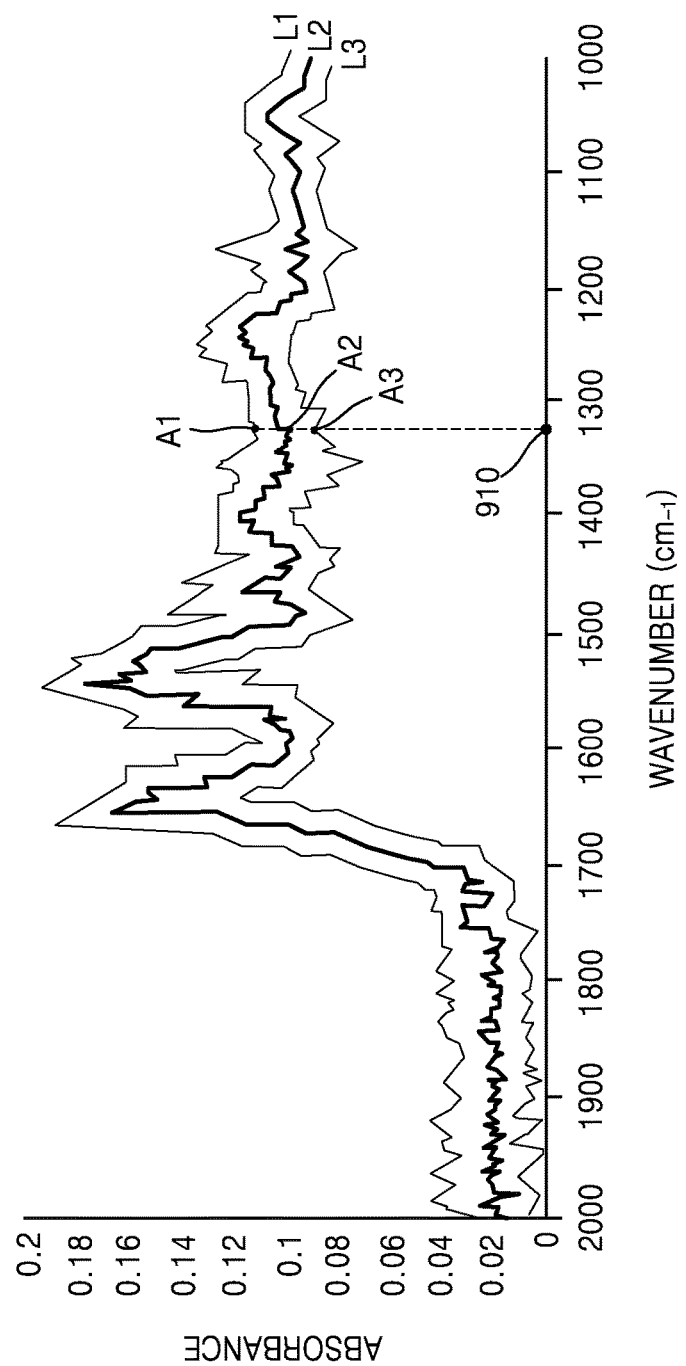
FIG. 10 is a view illustrating a result obtained after the light measurer performs absorption spectrum analysis a number of times on the same subject.

FIG. 10 is a view illustrating a result obtained after the light measurer 120 performs absorption spectrum analysis a number of times on the same subject 10. In FIG. 10, absorption spectrum curves L1, L2, and L3 are absorption spectrum curves obtained through different measurements.

Referring to FIG. 10, it is found that although an absorption spectrum of the same subject 10 is analyzed, absorbances slightly differ from one another. This is because of a change in a distance between the light source 110 and the subject 10, or when the light source 110 and the subject 10 contact each other, a change in a contact pressure and a change in an intensity of the light 20 that is emitted from the light source 110.

In order to reduce such a difference, normalization may be performed by dividing the absorbances of the absorption spectrum by an absorbance at a second wavenumber that is a reference wavenumber. The second wavenumber may be selected outside the first wavenumber range. In FIG. 10, for example, a wavenumber 910 of 1330 cm$^{-1}$ that is outside the first wavenumber range including the ranges 810, 820, 830, 840, and 850 (see FIG. 9) is selected as the second wavenumber. At the selected second wavenumber, the absorption spectrum curves L1, L2, and L3 respectively have absorbances A1, A2, and A3 at 1330 cm$^{-1}$. A normalized absorption spectrum curve may be obtained by respectively dividing absorbances of the absorption spectrum curves L1, L2, and L3 by the absorbances A1, A2, and A3.

Figure 11:
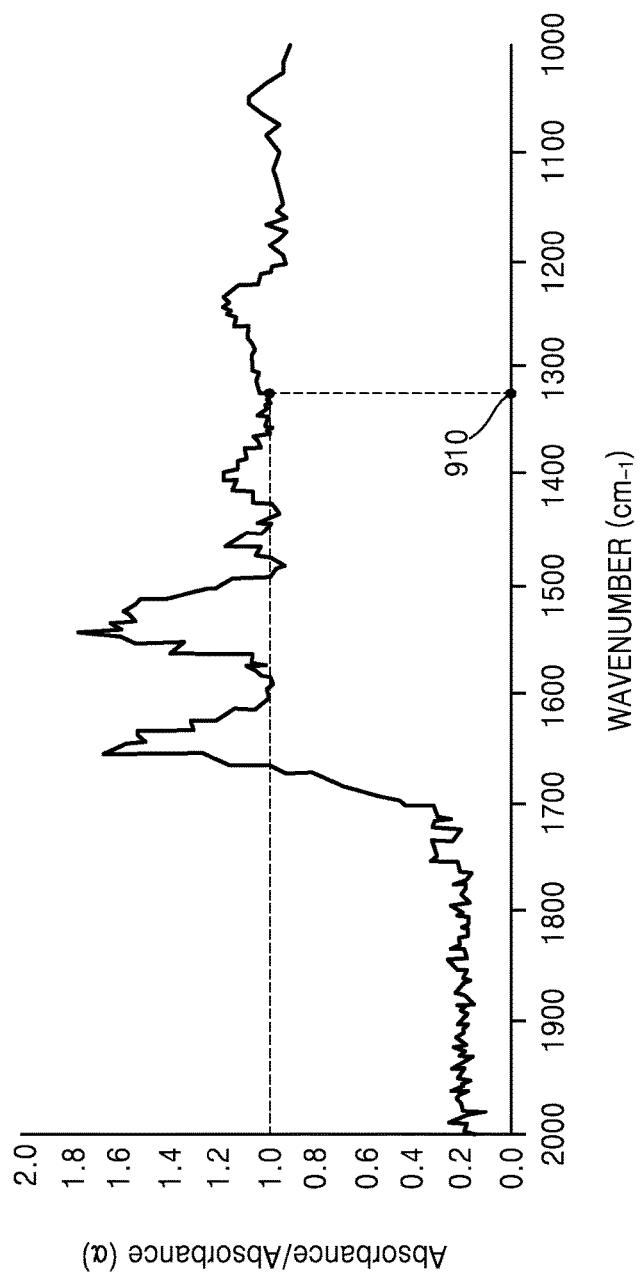
FIG. 11 is a view illustrating a result obtained by normalizing spectrum curves of FIG. 10.

FIG. 11 is a view illustrating a result obtained by normalizing spectrum curves of FIG. 10.

The data extractor 130 may normalize an absorption spectrum and may extract data from a result of the normalization as shown in FIG. 11.

Referring to FIG. 1, the data processor 140 may derive information about stress of the subject 10 by using a correlation between the data and the stress of the subject 10. For example, the stress of the subject 10 may refer to an average reference value of a stress hormone which is pre-measured from a plurality of saliva or blood samples of human subjects and saved in the data processor 140. The data processor 140 may calculate an amount of a stress hormone of the subject 10 based on the data and the reference value. To this end, the data processor 140 may store a correlation between the data and the reference value of the stress hormone. Also, as described above, the stress hormone may include cortisol.

Figure 12:
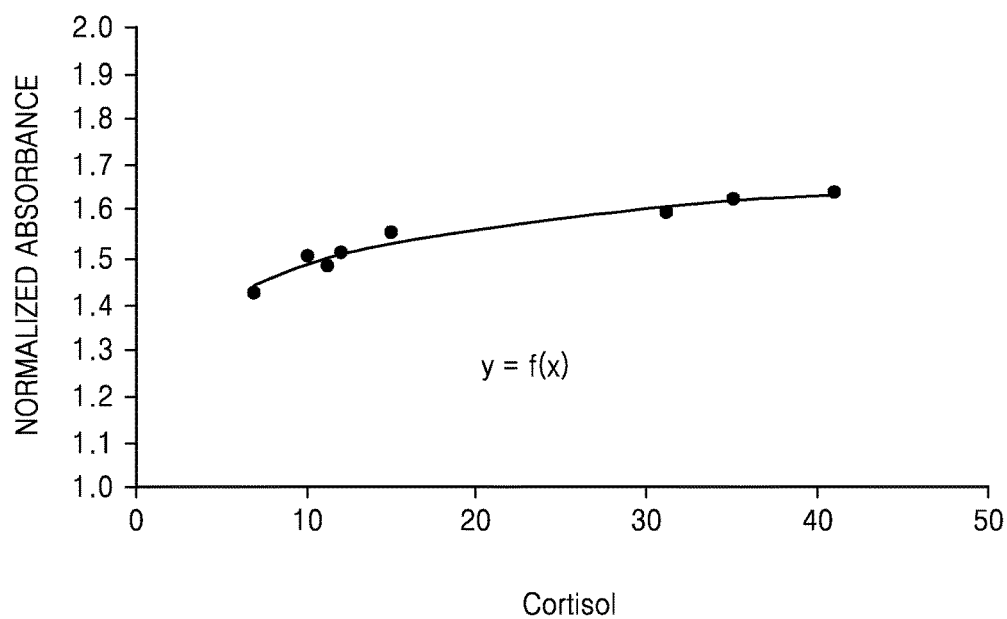
FIG. 12 is a graph illustrating a correlation between a data variable and a concentration of cortisol.

FIG. 12 is a graph illustrating a correlation between a data variable and a concentration of cortisol. The graph of FIG. 12 conceptually shows a relationship between the data variable and the concentration of cortisol, and a correlation derived according to the present exemplary embodiment may be different from the correlation shown in FIG. 12. The data variable may be determined by normalized absorbances in a first wavenumber range. For example, the data variable may be a normalized absorbance for any one peak value from among peak values in the first wavenumber range.

A correlation between data for at least one object material and information about stress may be defined in various ways. A correlation between data obtained by various combinations of one or more object materials and information about stress may be defined.

For example, the data variable may be a combination of absorbances of peaks in a specific wavenumber range. There are many methods of obtaining the combinations. For example, a y-axis variable of the graph of FIG. 12 may be a value obtained by adding absorbances of peaks included in a range from about 1640 $cm^{-1}$ to about 1690 $cm^{-1}$, a range from about 1550 $cm^{-1}$ to about 1640 $cm^{-1}$, a range from about 1050 $cm^{-1}$ to about 1150 $cm^{-1}$, a range from about 1735 $cm^{-1}$ to about 1750 $cm^{-1}$, and a range from about 1620 $cm^{-1}$ to about 1680 $cm^{-1}$. Alternatively, multiplication or any other mathematical operation, instead of addition, may be performed between absorbances of peaks, or absorbances of peaks in a specific range may be multiplied by their weights and then may be added. For example, absorbances of peaks of a wavenumber range corresponding to a functional group of hyaluronic acid whose change in a concentration is greatly affected by cortisol may be multiplied by relatively high weights. That is, absorbances of peaks in wavenumber ranges corresponding to a functional group C=O, a functional group N—H, and a functional group C—O that are included in hyaluronic acid may be multiplied by relatively high weights and then may be added. The method of setting the data variable is exemplary, and the present exemplary embodiment is not limited thereto.

Referring to FIG. 12, once the data variable is set as the y-axis variable, the data processor 140 may derive and store a correlation between the data variable and a concentration of cortisol. The correlation may be obtained by previously performing comparative experiments on a plurality of subjects. When the number of the comparative experiments increases, the accuracy of the correlation may increase. As data through the comparative experiments is accumulated, the data processor 140 may derive a correlation between the y-axis variable and an x-axis variable and may store the correlation. The data processor 140 may extract information about stress of the subject 10 based on the stored correlation and the data received from the data extractor 130.

The information about the stress extracted by the data processor 140 may be output in various ways. For example, the information about the stress may be a concentration of cortisol itself. Alternatively, the data processor 140 may previously define an appropriate correlation between a concentration of cortisol and a stress level and may quantitatively extract stress information. Alternatively, the data processor 140 may directly calculate a stress level from the data without calculating a concentration of cortisol. Even in this case, the correlation shown in FIG. 12 may be reflected and considered in an algorithm by which the data processor 140 calculates the stress level.

It has been described that the data extractor 130 extracts data from an absorption spectrum in FIGS. 9 through 12. However, the apparatus 100 of FIG. 1 is not limited thereto. For example, the data extractor 130 may use a Raman spectrum of the light 30 reflected from the subject 10. To this end, the light measurer 120 may measure the light 30 reflected from the subject 10 by using Raman spectroscopy.

In Raman spectroscopy, when the light 20 emitted from the light source 110 is incident on the subject 10, the light 20 may lose or obtain energy having a specific level in the subject 10. The specific level may vary according to, for example, a resonance frequency or structures of molecules in the subject 10. As the light 20 emitted from the light source 110 loses or obtains energy, part of the light 20 may be shifted, which is called a Raman shift. Accordingly, a wavelength of the light 30 reflected from the subject 10 may be a result obtained after a wavelength of part of the light 20 emitted from the light source 110 is shifted. Information that indicates an amount of a material included in the subject 10 may be extracted from a spectrum in which a Raman shift occurs.

In order to more effectively observe a Raman shift, the light source 110 may be a laser source. That is, the light source 110 may be a device that emits light having a single wavelength or a narrow range of wavelengths. However, the light source 110 is exemplary, and the present exemplary embodiment is not limited thereto. For example, the light source 110 may be a device that emits light showing a spectrum having a very sharp peak at a specific wavelength.

The light measurer 120 may measure the Raman spectrum of the light 30 reflected from the subject 10. In the Raman spectrum measured by the light measurer 120, peaks may be formed at points at which a wavelength of the light 20 emitted from the light source 110 is shifted. A wavelength that is shifted may vary according to a type of a chemical functional group of an object material that is included in the subject 10. Also, a spectrum intensity of each peak may vary depending on the amount of a chemical functional group corresponding to each peak.

The data extractor 130 may extract data from the Raman spectrum measured by the light measurer 120. The data extractor 130 may extract as data a spectrum intensity at a wavenumber obtained by Raman-shifting a wavenumber corresponding to the object material from a predetermined wavenumber of the light 20 emitted from the light source 110. The wavenumber corresponding to the object material may be determined according to a wavenumber shift that occurs due to the chemical functional group that is included in the object material. The spectrum intensity at the wavenumber obtained by Raman-shifting the wavenumber corresponding to the object material may depend on the amount of the object material that is included in the subject 10. The data extractor 130 may extract the spectrum intensity as data and may apply the data to the data processor 140.

The wavenumber corresponding to the object material may be determined in consideration of the chemical functional group included in the object material. For example, when the object material is hyaluronic acid, hyaluronic acid includes an amide group, a group C—O—C, a hydroxyl(ok) group (—OH), and a carboxyl group (—COOH) as shown in FIG. 5. Accordingly, a wavenumber that is shifted by each of the chemical functional group may be selected as the wavenumber corresponding to the object material. For example, a wavenumber of about 1625 $cm^{-1}$, 1418 $cm^{-1}$, or 642 $cm^{-1}$ may be selected as a wavenumber that is shifted due to the amide group. Also, a wavenumber of about 1125 $cm^{-1}$, 1045 $cm^{-1}$, 948 $cm^{-1}$, or 897 $cm^{-1}$ may be selected as a wavenumber that is shifted due to the group C—O—C. Also, a wavenumber of about 948 $cm^{-1}$ or 897 $cm^{-1}$ may be selected as a wavenumber that is shifted due to the hydroxyl group. Also, a wavenumber of about 1625 $cm^{-1}$ may be selected as a wavenumber that is shifted due to the carboxyl group.

The apparatus 100 of FIG. 1 has been described in detail. Elements that the apparatus 100 of FIG. 1 may further include will be explained.

Figure 13:
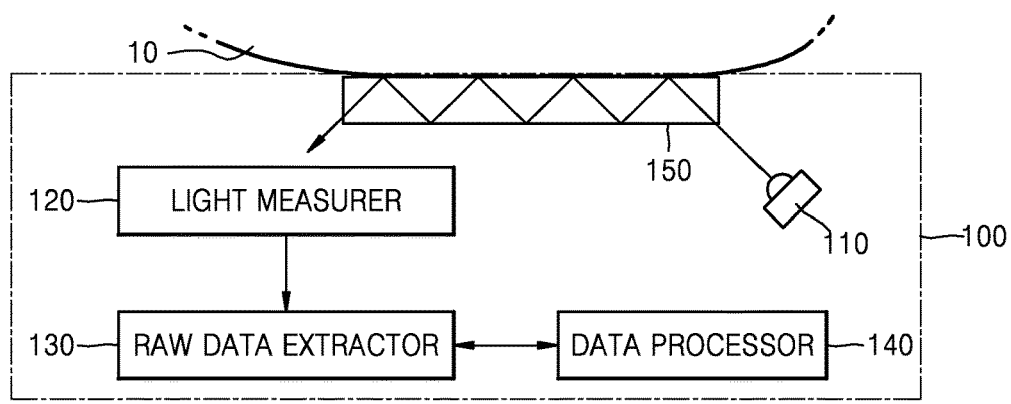
FIG. 13 is a view illustrating a case in which an attenuated total reflectance (ATR) layer is included in the apparatus.

FIG. 13 is a view illustrating a case in which an attenuated total reflectance (ATR) layer 150 is included in the apparatus 100.

Referring to FIG. 13, the apparatus 100 of FIG. 1 may further include the ATR layer 150 that is disposed between the light source 110 and the subject 10. The apparatus 100 may perform ATR to analyze an absorption spectrum of the subject 10 by using the ATR layer 150. The ATR layer 150 may be a layer formed of a transparent material having a high refractive index such as quartz. The ATR layer 150 is exemplary, and the present exemplary embodiment is not limited thereto. A surface of the ATR layer 150 may contact the subject 10 as shown in FIG. 13. An angle at which the light 20 is incident on the ATR layer 150 may be appropriately adjusted so that total reflection occurs on the ATR layer 150.

Figure 14:
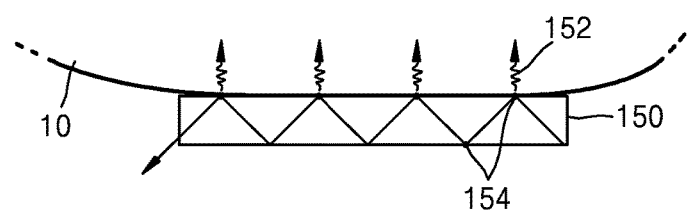
FIG. 14 is a view for explaining an ATR process.

FIG. 14 illustrates an ATR process.

As shown in FIG. 14, light may be totally reflected at many points 154 of the ATR layer 150. During the total reflection, an evanescent wave may be transmitted from a contact surface between the subject 10 and the ATR layer 150 into the subject 10. Although the evanescent wave is incident into the subject 10, an intensity of the evanescent wave may be exponentially attenuated as a depth in the subject 10 increases. Light that is totally reflected due to absorption of the evanescent wave reflects absorption characteristics of the subject 10. As total reflection increases, absorption characteristics of the subject 10 may be more accurately reflected, and thus the ATR layer 150 may amplify a spectrum signal.

Figure 15:
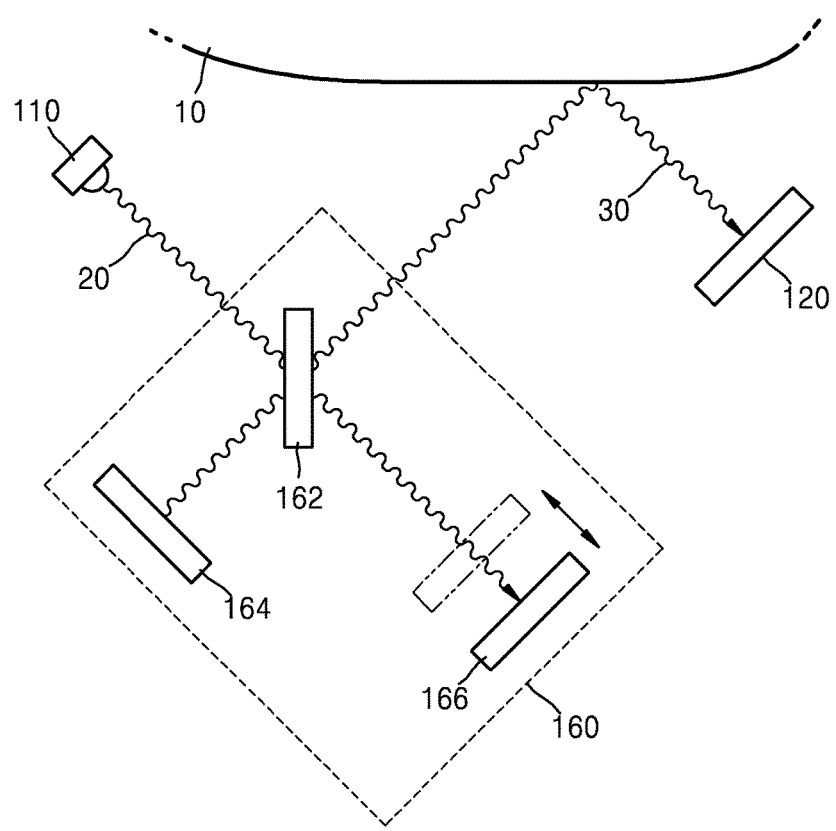
FIG. 15 is a view illustrating a case in which an interferometer is further included in optical system represented in FIG. 1.

FIG. 15 is a view illustrating a case in which an interferometer 160 is further included in optical system represented in FIG. 1.

Referring to FIG. 15, the light source 110, the light measurer 120, and the interferometer 160 may implement a Fourier transform-infrared (FT-IR) spectrometer. The interferometer 160 may be disposed between the light source 110 and the subject 10 and may change a spectrum of the light 20 that is incident on the subject 10 from the light source 110. The apparatus 100 may perform FT-IR spectroscopy to measure an absorption spectrum of the subject 10 by using the interferometer 160. Noise may be reduced when the FT-IR spectroscopy is used. That is, a signal-to-noise ratio may be increased during spectrum analysis.

The interferometer 160 may include a beam splitter 162, a first mirror 164 that is fixed, and a second mirror 166 that is movable, as shown in FIG. 15. The light 20 that is emitted from the light source 110 may be incident on the beam splitter 162. Part of the light 20 may be reflected by the beam splitter 162 to the first mirror 164, and remaining part of the light 20 may pass through the beam splitter 162 and may be incident on the second mirror 166. A spectrum of light that is incident from the beam splitter 162 on the subject 10 may be changed due to interference between light that is reflected by the first mirror 164 and light that is reflected by the second mirror 166. A spectrum of the light that is incident on the subject 10 may be changed in various ways by changing an interference condition by changing a position of the second mirror 166.

An absorption spectrum in the subject 10 may be calculated by checking how a spectrum of the light 30 reflected from the subject 10 is changed with respect to the spectrum of the incident light 20 that is changed as described above. Fourier transform may be used during a process of calculating the absorption spectrum in the subject 10, and the calculation may be performed by the light measurer 120. Alternatively, the calculation may be performed by another element, for example, the data extractor 130. The interferometer 160 of FIG. 15 is exemplary, and any device for changing a spectrum of the light 20 that is incident on the subject 10 may be used in the exemplary embodiment.

Although each element of the apparatus 100 is independently illustrated in FIG. 1, it does not mean that each element is separated as hardware. For example, although the data extractor 130 and the data processor 140 are illustrated as separate elements in FIG. 1, the data extractor 130 and the data processor 140 may be provided as one micro control unit (MCU). Accordingly, any device manufactured to perform a function of each element of FIG. 1 may be used.

Also, the apparatus 100 of FIG. 1 may be used in various applications. The apparatus 100 may be applied to a medical device, a biological analysis device, etc. In addition, the apparatus 100 may be applied to a health care device due to its compact design. Accordingly, the apparatus 100 may be coupled to a portable device or a wearable device and may noninvasively check a stress level of a user at any time.

The apparatus 100 has been explained with reference to FIGS. 1 through 15. A method of measuring stress according to an exemplary embodiment will now be explained. The technical descriptions of the apparatus 100 may apply to the method.

Figure 16:
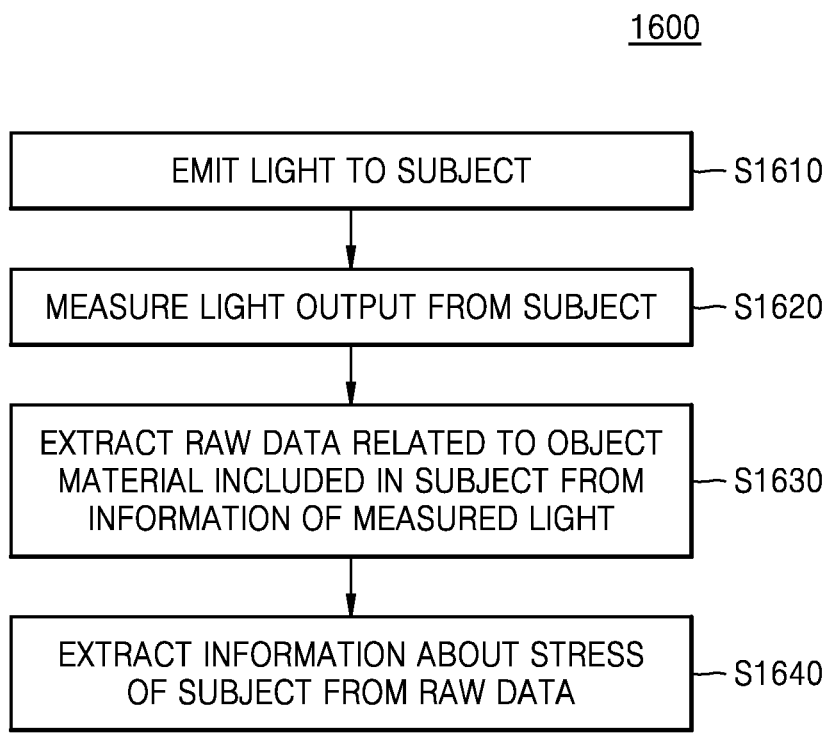
FIG. 16 is a flowchart illustrating a method of measuring stress, according to an exemplary embodiment.

FIG. 16 is a flowchart illustrating a method 1600 of measuring stress, according to an exemplary embodiment.

Referring to FIGS. 1 and 16, the method 1600 may include operation S1610 in which the light source 110 emits the light 20 to the subject 10, operation S1620 in which the light 30 reflected from the subject 10 is measured, and operation S1630 in which data related to at least one object material included in the subject 10 is extracted from information measured in operation S1620. The method 1600 may further include operation S1640 in which information about stress of the subject 10 is extracted by using a correlation between the data and the stress of the subject 10.

A wavelength band of the light may include a mid-infrared range, for example, a range from about 2.5 µm to about 20 µm. The present exemplary embodiment is not limited thereto, and a near-infrared range or other wavelength ranges may be used as described above.

The object material may include at least one selected from hyaluronic acid, triglyceride, wax ester, and squalene. The object material is not limited thereto, and an amount of each component included in the object material may change in accordance with a stress level of the subject 10.

Operation S1620 may include an operation in which the light 30 reflected from the subject 10 is separated according to wavelengths and an operation in which an intensity of the separated light is measured according to wavelengths. In operation S1620, an absorption spectrum of the subject 10 may be analyzed from the light 30 reflected from the subject 10.

Operation S1630 may include an operation in which absorbances of light in a first wavenumber range corresponding to the at least one object material are extracted from the absorption spectrum. The first wavenumber range may include at least one selected from a range from about 1640 cm$^{-1}$ to about 1690 cm$^{-1}$, a range from about 1550 cm$^{-1}$ to about 1640 cm$^{-1}$, a range from about 1050 cm$^{-1}$ to about 1150 cm$^{-1}$, a range from about 1735 cm$^{-1}$ to about 1750 cm$^{-1}$, and a range from about 1620 cm$^{-1}$ to about 1680 cm$^{-1}$.

Operation S1630 may include an operation in which normalization is performed by dividing the absorbances of the light in the first wavenumber range by an absorbance at a second wavenumber that is outside the first wavenumber range.

Operation S1640 may include an operation in which the correlation between the data and information about the stress of the subject is stored. For example, operation S1640 may include an operation in which a correlation between the data and a hormone released due to the stress is stored.

The method 1600 may use a Raman spectrum of light, instead of the absorption spectrum. In this case, in operation S1630, an intensity of the Raman spectrum may be extracted at a wavenumber obtained by Raman-shifting a wavenumber corresponding to the object material from a wavenumber of the light 20 that is emitted from the light source 110. The wavenumber corresponding to the object material may include at least one selected from about 1625 cm$^{-1}$, 1418 cm$^{-1}$, 642 cm$^{-1}$, 1125 cm$^{-1}$, 1045 cm$^{-1}$, 948 cm$^{-1}$, 897 cm$^{-1}$, and 1625 cm$^{-1}$.

When the ATR layer 150 is used as described with reference to FIGS. 13 and 14, the method 1600 may further include an operation in which the light 30 reflected from the subject 10 is totally reflected by the ATR layer 150. When FT-IR spectroscopy using the interferometer 160 is used as shown in FIG. 15, the method 1600 may further include an operation in which a spectrum of the light 20 that is emitted from the light source 110 is changed by using the interferometer 160. The apparatus 100 may noninvasively measure stress of the subject 10. Information about the stress of the subject 10 may be output through optical analysis performed on the subject 10.

The foregoing exemplary embodiments are merely exemplary and are not to be construed as limiting. The present disclosure can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for measuring stress of a subject, the apparatus comprising:
    a light source configured to emit light to the subject;
    a sensor configured to measure light reflected from the subject;
    a data extractor configured to obtain, from a spectrum of the reflected light, an absorbance of light in a first wavenumber range corresponding to at least one object material, the first wavenumber range comprising at least one selected from a range from about 1640 cm$^{-1}$ to about 1690 cm$^{-1}$, a range from about 1550 cm$^{-1}$ to about 1640 cm$^{-1}$, a range from about 1050 cm$^{-1}$ to about 1150 cm$^{-1}$, a range from about 1735 cm$^{-1}$ to about 1750 cm$^{-1}$, and a range from about 1620 cm$^{-1}$ to about 1680 cm$^{-1}$; and
    a data processor configured to generate information about the stress of the subject based on a correlation between the absorbance of the light in the first wavenumber range corresponding to the at least one object material and a reference value of the stress.

2. The apparatus of claim 1, wherein the emitted light has a wavelength within a range between about 2.5 μm and 20 μm.

3. The apparatus of claim 1, wherein the sensor is further configured to measure the spectrum of the light reflected from the subject.

4. The apparatus of claim 1, wherein the at least one object material comprises at least one among hyaluronic acid, triglyceride, wax ester, and squalene.

5. The apparatus of claim 1, wherein the data extractor is further configured to perform normalization by dividing the absorbance of the light in the first wavenumber range by an absorbance at a second wavenumber that is outside the first wavenumber range.

6. The apparatus of claim 1, wherein the reference value corresponds to a level of a hormone released by a living body under the stress.

7. The apparatus of claim 6, wherein the hormone comprises cortisol.

8. The apparatus of claim 1, wherein the data extractor is further configured to obtain an intensity of the spectrum of the reflected light at a wavenumber obtained by Raman-shifting a wavenumber corresponding to the at least one object material.

9. The apparatus of claim 8, wherein the wavenumber corresponding to the at least one object material comprises at least one selected from about 1625 cm$^{-1}$, 1418 cm$^{-1}$, 642 cm$^{-1}$, 1125 cm$^{-1}$, 1045 cm$^{-1}$, 948 cm$^{-1}$, and 897 cm$^{-1}$.

10. The apparatus of claim 1, further comprising an attenuated total reflectance (ATR) layer on which the light emitted from the light source is incident and reflected.

11. The apparatus of claim 1, wherein the sensor comprises:
    a spectrometer configured to separate the reflected light according to wavelengths; and
    a detector configured to measure an intensity of the separated light.

12. The apparatus of claim 1, wherein the sensor comprises a Fourier transform-infrared (FT-IR) spectrometer.

13. The apparatus of claim 1, wherein a level of a hormone released by a living body under the stress is pre-measured from a plurality of subjects and a correlation between the absorbance of the light in the first wavenumber range corresponding to the at least one object material and the level of the hormone is pre-stored in the data processor.

14. The apparatus of claim 13, wherein the data processor is configured to generate the information about the stress of the subject based on the correlation between the absorbance of the light in the first wavenumber range corresponding to the at least one object material and the level of the hormone.

15. A method of measuring stress of a subject, the method comprising:

emitting light from a light source to the subject;
measuring light reflected from the subject;
obtaining, from a spectrum of the reflected light, an absorbance of light in a first wavenumber range corresponding to at least one object material, the first wavenumber range comprising at least one selected from a range from about 1640 $cm^{-1}$ to about 1690 $cm^{-1}$, a range from about 1550 $cm^{-1}$ to about 1640 $cm^{-1}$, a range from about 1050 $cm^{-1}$ to about 1150 $cm^{-1}$, a range from about 1735 $cm^{-1}$ to about 1750 $cm^{-1}$, and a range from about 1620 $cm^{-1}$ to about 1680 $cm^{-1}$; and
generating information about the stress of the subject based on a correlation between the absorbance of the light in the first wavenumber range corresponding to the at least one object material and a reference value of the stress.

16. The method of claim 15, wherein the at least one object material comprises at least one among hyaluronic acid, triglyceride, wax ester, and squalene.

17. The method of claim 15, wherein the reference value corresponds to a hormone released by a living body under the stress, and the hormone comprises cortisol.

18. The method of claim 15, wherein the measuring of the light reflected from the subject comprises measuring the spectrum of the light reflected from the subject, and the obtaining of the absorbance of the light in the first wavenumber range corresponding to the at least one object material comprises obtaining an intensity of the spectrum at a wavenumber obtained by Raman-shifting a wavenumber corresponding to the at least one object material.

19. The method of claim 18, wherein the wavenumber corresponding to the at least one object material comprises at least one selected from about 1625 $cm^{-1}$, 1418 $cm^{-1}$, 642 $cm^{-1}$, 1125 $cm^{-1}$, 1045 $cm^{-1}$, 948 $cm^{-1}$, and 897 $cm^{-1}$.

* * * * *